United States Patent
Dougherty

(12) 
(10) Patent No.: US 6,423,753 B1
(45) Date of Patent: Jul. 23, 2002

(54) USE OF COLCHINOL DERIVATIVES AS VASCULAR DAMAGING AGENTS

(75) Inventor: Graeme Dougherty, Edinburgh (GB)

(73) Assignee: Angiogene Pharmaceuticals Ltd., Oxfordshire (GB)

( * ) Notice: Subject to any disclaimer, the term of this patent is extended or adjusted under 35 U.S.C. 154(b) by 0 days.

(21) Appl. No.: 09/477,805

(22) PCT Filed: Jul. 6, 1998

(86) PCT No.: PCT/GB98/01977

§ 371 (c)(1),
(2), (4) Date: Jan. 5, 2000

(87) PCT Pub. No.: WO99/02166

PCT Pub. Date: Jan. 21, 1999

(30) Foreign Application Priority Data

Jul. 8, 1997 (GB) .............................................. 9714249

(51) Int. Cl.[7] .................... A61K 31/075; A61K 31/045; C07C 39/12; C07C 41/00

(52) U.S. Cl. ........................ 514/719; 514/721; 514/729; 568/733; 568/660

(58) Field of Search ................................ 568/733, 660; 514/719, 721, 729

(56) References Cited

U.S. PATENT DOCUMENTS

| | | | |
|---|---|---|---|
| 3,442,953 A | * | 5/1969 | Muller et al. ................ 568/733 |
| 5,561,122 A | | 10/1996 | Pettit |
| 5,760,092 A | | 6/1998 | Timasheff et al. |
| 5,843,910 A | | 12/1998 | Bombardelli et al. |
| 5,880,160 A | | 3/1999 | Bombardelli et al. |
| 5,973,204 A | * | 10/1999 | Bombardelli ................ 564/222 |
| 6,080,739 A | * | 6/2000 | Bombardelli ............ 514/229.5 |

FOREIGN PATENT DOCUMENTS

| | | |
|---|---|---|
| FR | 4.685 M | 7/1965 |
| JP | 39-19634 | 9/1964 |
| JP | 39-19635 | 9/1964 |
| WO | WO 97/47577 | 12/1997 |
| WO | WO 00/40529 | 7/2000 |
| WO | WO 00/48606 | 8/2000 |

OTHER PUBLICATIONS

Boyé et al., "Natural Products. Antitubulin effect of congeners of N–acetylcolchinyl methyl ether: . . . of demethoxy analogues of deaminocolchinyl methyl ether"; Can. J. Chem., vol. 70, 1992, pp. 1237–1249.

Boyé et al., "Potential Covalent Markers of the Colchincine–Binding–Site . . . with Isothiocyanato Groups", Med. Chem. Res. 1991, pp. 142–150.

Brecht et al., "(–)–(M,7S) Colchine and (–)–(M, 7S)–10–Ethylthiocolchide/Alkyne . . . Consecutive [4,30 2] and [3+2] Cycloadditions", Eur. J. Org. Chem. 1998, pp. 2451–2460.

Brossi et al., "aS,7S–absolute configuration of natural (–)–colchine and allocongeners", FEBS Letters, 1990, vol. 62, No. 1, pp. 5–7.

Deinum et al., "Synthesis and Binding to Tubulin of an Allocolchicine Spin Probe", Acta Chemica Scandinavica B, 1981, B35, No. 10, pp. 677–681.

Dilger et al., "Arbeitsvorschriften und Meβwerte—Procedures and Data Formaldehyd–O–oxid . . . Allocolchincinen", J. Prakt/Chem–Ztg, 1998, pp. 468–471.

Ghera et al., "Total Synthesis of the Lignan (±)–Schizandrin"; J.C.S. Chem. Comm., 1978, pp. 480–481.

Hahn et al., "Synthesis and Evaluation of . . . Photochemistry, and Tubulin Binding", Photochem Photobiol. 1992, vol. 55, No. 1, pp. 17–27.

Hrbek et al., Circular Dichrosim of Alkaloids of Colchine Type and their Derivatives, Collect. Czech. Chem. Commun, 1982, vol. 47, No. 8, pp. 2258–2279.

(List continued on next page.)

Primary Examiner—Deborah C. Lambkin
(74) Attorney, Agent, or Firm—Morgan, Lewis & Bockius LLP

(57) ABSTRACT

Colchinol derivatives of formula

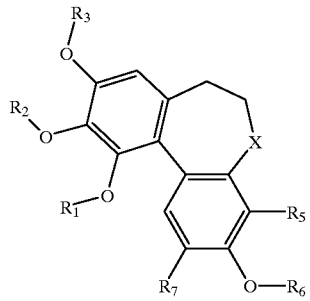

(I)

wherein $R_1$, $R_2$, $R_3$ and $R_6$ are each independently H, optionally substituted alkyl, cycloalkyl, alkenyl, alkynyl, aralkyl, alkanoyl, $PO_3H_2$; X is carbonyl (CO), thiocarbonyl (CS), methylene ($CH_2$) or a group $CHR_4$; $R_4$ is OH, O-alkyl or $NR_8R_9$; $R_5$ and $R_7$ are each independently H, alkyl, halogen, hydroxy, alkoxy, nitro or amino; $R_8$ is H, optionally substituted alkyl, cycloalkyl, alkanoyl, thioalkanoyl, aryl, heteroaryl, arylcarbonyl, heteroarylcarbonyl, alkoxycarbonyl, aryloxycarbonyl, aminocarbonyl, alkylaminocarbonyl, dialkylaminocarbonyl, arylaminocarbonyl, alkylsulphonyl, arylsulphonyl, aminosulphonyl, alkylaminosulphonyl, dialkylaminosulphonyl or arylaminosulphonyl; and $R_9$ is H, alkyl or cycloalkyl; and the pharmaceutically acceptable salts, solvates, and hydrates thereof have been found to be useful for treatment of diseases involving angiogenesis. Some of these compounds are novel. Particularly preferred are those compounds in which $R_6$ is $PO_3H_2$.

16 Claims, No Drawings

OTHER PUBLICATIONS

Hunter et al., "The photo–oxidation of some novel Colchine derivatives", Afinidad, vol., 38, No. 372, 1981, pp. 122–123.

Iorio, "Contraction of the Tropolonic Ring of Colchine by Hydrogen Peroxide Oxidation", Heterocycles, vol., 22, No. 10, 1984, pp. 2207–2211.

Kiselev et al., "Benzenoid Rearrangement of Colchine by the Action of Ethylene Glycol", Plenum Publishing Corp., 1978 pp. 2175–2179.

Kita et al., "Non–phenolic oxidative coupling of phenol ether derivatives using phenyliodine(III) bis(trifluoroacetate)", Chem. Commun., 1996, pp. 1481–1482.

Leiter et al., "Damage Induced in Sarcoma 37 with . . . Trimethylcolchinic Acid and to Colchinol", J. Nat. Cancer Inst., 1952, pp. 379–392.

Mackay et al, "Structures of Colchinine Analogues . . . $C_{20}H_{22}Br_2N_2O_4$", Acta Crystallogr, Section C: Cryst. Struct Commun, 1991, C47 (12), pp. 2615–2618.

Olszewski et al., Potential Photoaffinity Labels for Tubulin . . . Colchicine, Combretastatin, and 3,4,5–Trimethoxybiphenyl: J. Org. Chem, 1994, 59 (15) 4285–4296.

Palmquist et al., "Anodic Oxidation of Phenolic Compounds . . . Coupling of Phenolic Diarylakanes"; J Am Chem Soc., 1976, 98(9), 2571–2580.

Pyles et al, "Role of the B–ring Substituent in the Fluorescence of Colchicinoid–Tubulin and Allcolchicinoid–Tublin Complexes", Biochemistry, vol. 31, No. 31, 1992, pp. 7086–7093.

Schönharting et al., "I. The Oxidative Formation of Products from Colchicine in the Udenfriend System", Hoppe–Seyler's Z. Physiol Chem., 1973, 354 (1), pp. 421–436.

Shi et al., "Antitumor Agents. 172. Synthesis and Biological Evaluation . . . and Ester Analogs as Antitubulin Agents", J. Med. Chem., 1997, 40, pp. 961–966.

Shi et al., "Antitumor Agents. 183. Syntheses, Conformational Analyses, and Antitubulin Activity of Allothiocolchicinoids", J. Org. Chem, 1998, 63, pp. 4018–4025.

Shi et al., "Antitumor Agents, Part 184, Syntheses and Antitubulin Activity . . . Analogs of Allothiocolchicinoids", Helvetica Chimica Acta, vol. 81, 1998, pp. 1023–1037.

Staretz et al., "Synthesis, Photochemical Decompositions, and . . . 9–Azido–9–demethoxyisocolchine"; J Org Chem, 1991, 56 (1), pp. 428–432.

Šterzl et al., "Effect of Colchine Derivatives on the Antibody Response Induced in vitro", Folia Microbiol. (Prague), 1982, 27 (4), pp. 256–266.

Tang–Wai et al., "Structure Activity Relationships in the Colchicine . . . Transporter, P–Glycoprotein", Heterocycles, 1994, vol. 39, No. 1, pp. 385–403.

Timbekov et al., "Mass–Spectrometric Study of New Alkaloids from Plants of the Family Liliaceae", Plenum Publishing Corporation, 1985, pp. 1–9.

Tojo et al., "The Dibenzocycloheptylamine Alkaloids", J Nat Prod., 1989, 52 (5), pp. 1163–1166.

Wolff et al., "Colchicine Binding to Antibodies", The Journal of Biological Chemistry, 1980, vol. 255, No. 15, pp. 7144–7148.

Wosikowski et al., Identification of Epidermal Growth . . . Gene Expression Patterns, J Natl Cancer Inst., 1997, 89 (20) pp. 1505–1515.

Xie et al., "Synthesis of three new Schizandrin Analogues", Chin. Chem. Letters, vol. 9, No. 7, 1998, pp. 621–634.

Yusupov et al, "A Study of 2–Demethyllallocolchine and Its Derivatives" Plenum Publishing Company, 1975, pp. 188–191.

Zarga et al., "New Natural Dibenzocycloheptylamine Alkaloids: A Possible Catabolic Route for the Colchine Alkaloids"; J. Nat. Prod, 1991, 54(4), pp. 936–40.

Izv Akad Nauk Turkm SSR, Ser Fiz–Tekh, Khim Geol Nauk (1976), (1), pp. 70–73 (in Russian).

Zh. Obshch Khim (1970), 40 (4), pp. 914–915 (in Russian).

Zh. Obshch. Khim (1971), 41 (2) pp. 464–466 (in Russian).

O. Boye et al: "Synthesis of carbon–14labeled electrophilic ligands of the colchicine binding site of tubulin: chloroacetates of demethylthiocolchicines and of N–acetylcolchinol, isothiocynanates of 9–deoxy–N–acetylcolchinol" J. Labelled Compd. Radiopharm., vol. 33, No. 4, 1993, pp. 293–299, XP002081866.

R.Brecht et al.: "Dihydrocolchicine 8, 12–endoperoxide. a novel starting material for convenient syntheses of the allocolchicinoids N–acetylcolchinol O–methyl ether and androbiphenyline." Liebigs Ann., No. 11, 1997, pp. 2275–2279, XP002081867.

Gil–Jong Kang et al: "n–acetylcolchinol O–methyl ether and thiocolchicine, potent nalogs of colchicine modified in the C–ring" J.Biol. Chem., vol. 265, No. 18, 1990, pp. 10255–10259, XP002081868.

Al–Tel et al., "New Natural Colchcicinoids: Indications of . . . for the Colchine Alkaloids", Journal of Natural Products, vol. 53, No. 3, May–Jun., 1990, pp. 623–629.

Banwell et al., "Synthesis and Tubulin–Binding Properties of Some AC– and ABC–Ring Analogues of Allocolchicine", Aust. J. Chem., 1992, vol. 45, No. pp. 1967–1982.

Banwell et al., "Total Synthesis of the Structure . . . *Colchicum decaisnei* Bioss. (Liliaceae)", J. Chem. Soc., Chem. Comm., 1994 pp. 2647–2649.

Battersby et al., "Biosynthesis. Part 26.[1] Synthetic Studies on Structural Modification of Late Biosynthetic Precursors for Colchicine"; J. Chem. Soc., Perkin Trans. 1, 1983, pp. 3053–3063.

Boger et al., "Thermal Reactions of Cyclopropenone Ketals . . . Totally Synthesis of Colchicine", J. Am. Chem. Soc., 1986, 108, pp. 6713–6719.

Boyé et al., "185. Deaminocolchinyl Methyl Ether: Synthesis . . . Effects of Deaminocolchinyl Methyl Ether and Dehydro Analogs", Helvetica Chimica Acta, vol. 72, 1989, pp. 1690–1696.

Kiselev, "Derivatives of Aminocolchicide", Translation of Zh. Obshch Khim (1970), 40 (4), pp. 914–915, Russian Language original cited on page 3 of Form PTO–1449 dated Aug.21, 2001.

Kiselev, "Derivitives of Aminoclochicidek VII", Translation of Zh.Obshch, Khim (1971), 41, (2) pp. 464–466, Russian Language origingal Cited on page 3 of Form PTO 1449 dated Aug. 21, 2001.

* cited by examiner

USE OF COLCHINOL DERIVATIVES AS VASCULAR DAMAGING AGENTS

This application is the national phase of international application PGT/GB98/01977 filed Jul. 6. 1998 which designated the U.S.

This invention relates to vascular damaging agents and particularly to use in the preparation of agents for treatment of neovascularisation of a group of colchinol derivatives some of which are new compounds.

Formation of new vasculature by angiogenesis is a key pathological feature of several diseases (J Folkman, New England Journal of Medicine 333, 1757 (1995)). For example, for a solid tumour to grow it must develop its own blood supply upon which it depends critically for the provision of oxygen and nutrients; if this blood supply is mechanically shut off the tumour undergoes necrotic death. Neovascularisation is also a clinical feature of skin lesions in psoriasis, of the invasive pannus in the joints of rheumatoid arthritis patients and of atherosclerotic plaques. Retinal neovascularisation is pathological in macular degeneration and i diabetic retinopathy. In all these diseases reversal of neovascularisation by damaging the newly-formed vascular endothelium is expected to have a beneficial therapeutic effect.

Colchinol derivatives for example N-acetyl-colchinol are known. Anti-tumour effects have been noted on animal models (see for example—JNCI (Journal National Cancer Institute) Page 379–392 1952, Vol 13). However, the effect studied was that of gross damage (haemorrhage, softening and necrosis) and there is no suggestion of treatment of inappropriate angiogenesis by destruction of neovasculature.

A search of Chemical Abstracts (post 1955) based on the substructure

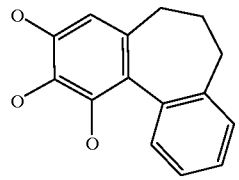

revealed a number of colchinol related structures.

To the extent that any of these compounds have been studied for anti-cancer activity it is because tubulin binding agents might be expected to be anti-mitotic and therefore to have a direct effect on tumour cells.

In the course of the work on the present invention, the issue of the relevance of tubulin-binding properties to possible effectiveness as anti-vascular agent was studied but no predictability was found. Thus docetaxel (Lancet, 344, 1267–1271, 1994), which is a tubulin-binding agent, had no vascular-damaging effects even when administered at its Maximum Tolerated Dose. Even when the present inventors tested some compounds structurally related to the present invention, the therapeutic window (ratio of MTD (Maximum tolerated dose) to MED (Minimum effective dose)) was found to be too small for potential clinical effectiveness.

According to the present invention there is provided the use of colchinol derivatives for the preparation of compositions for the treatment of diseases involving angiogenesis in which the colchinol derivative has the formula

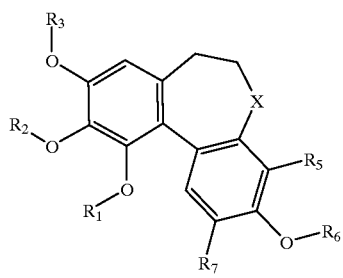

wherein
$R_1$, $R_2$, $R_3$ and $R_5$ are each independently H. optionally substituted alkyl, cycloalkyl, alkenyl, alkynyl, aralkyl, alkanoyl, $PO_3H_2$;
X is carbonyl (CO), thiocarbonyl (CS), methylene ($CH_2$) or a group $CHR_4$
$R_4$ is OH, O-alkyl or $NR_8R_9$;
$R_5$ and $R_7$ are each independently H, alkyl, halogen, hydroxy, alkoxy, nitro or amino;
$R_8$ is H, optionally substituted alkyl, cycloalkyl, alkanoyl, thioalkanoyl, aryl, heteroaryl, arylcarbonyl, heteroarylcarbonyl, alkoxycarbonyl, aryloxycarbonyl, aminocarbonyl, alkylaminocarbonyl, dialkylaminocarbonyl, arylaminocarbonyl, alkylsulphonyl, arylsulphonyl, aminosulphonyl, alkylaminosulphonyl, dialkylaminosulphonyl or arylaminosulphonyl;
and $R_9$ is H, alkyl or cycloalkyl
and the pharmaceutically acceptable salts, solvates, and hydrates thereof.

It is believed, though this is not limiting on the invention, that the use of compounds of the invention damages newly-formed vasculature, for example the vasculature of tumours, thus effectively reversing the process of angiogenesis as compared to known anti-angiogenic agents which tend to be less effective once the vasculature has formed.

Certain of these compounds are novel. In one embodiment the novel compounds are those of formula I in which at least one of $R_1$, $R_2$, $R_3$, $R_6$ is $PO_3H_2$. In a particular preferred embodiment $R_6$ is $PO_3H_2$. Particularly preferred are compounds defined by the formula

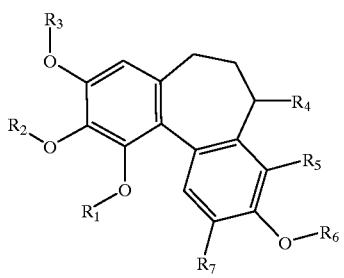

wherein
$R_1$, $R_2$ and $R_3$ are each independently H, optionally substituted alkyl, cycloalkyl, alkenyl, alkynyl, alkanoyl, or $PO_3H_2$;
$R_6$ is $PO_3H_2$;
$R_4$ is H or $NR_8R_9$;
$R_5$ and $R_7$ are each independently H, alkyl, halogen, alkoxy, nitro or amino;

R₈ is H, optionally substituted alkyl, cycloalkyl, alkanoyl, thioalkanoyl, aryl, heteroaryl, arylcarbonyl, heteroarylcarbonyl, alkoxycarbonyl, aryloxycarbonyl, aminocarbonyl, alkylaminocarbonyl, dialkylaminocarbonyl, arylaminocarbonyl, alkylsulphonyl, arylsulphonyl, aminosulphonyl, alkylaminosulphonyl, dialkylaminosulphonyl or arylaminosulphonyl;

and R₉ is H, alkyl or cycloalkyl, and the pharmaceutically acceptable salts, solvates and hydrates thereof.

In another aspect of the invention the novel compounds are of formula

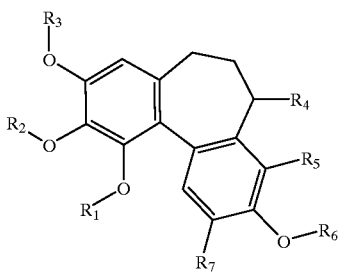

IIA wherein

R₁, R₂ and R₃ are each independently H, optionally substituted alkyl, cycloalkyl, alkenyl, alkynyl, alkanoyl or PO₃H₂;

R₆ is H, optionally substituted alkyl, cycloalkyl, alkenyl, akynyl or PO₃H₂;

R₄ is H or NR₈R₉;

R₅ and R₇ are each independently H, alkyl halogen, nitro or amino;

R₈ is H, optionally substituted alkyl, cycloalkyl, alkanoyl, thioalkyl, aryl, heteroaryl, arylcarbonyl, heteroarylcarbonyl, alkoxycarbonyl, aryloxycarbonyl, aminocarbonyl, alkylaminocarbonyl, dialkylaminocarbonyl, arylaminocarbonyl, alkylsulphonyl, arylsulphonyl, aminosulphonyl, alkylaminosulphonyl, dialkylaminosulphonyl or arylaminosulphonyl;

and R₉ is H, alkyl or cycloalkyl, with the proviso that, when R₁, R₂ and R₃ are all methyl groups and R₄ is hydrogen, acetylamino, acetylmethylamino, amino, methylamino or dimethylamino then R₆ is not hydrogen, methyl or hydroxyethyl, or acetoxyethyl, and the pharmaceutically acceptable salts, solvates and hydrates thereof.

Preferred compounds used in the invention and of the invention are those in which R₁, R₂ and R₃ are alkyl and those in which R₄ is acylamino.

As used herein the term "alkyl", (including any aliphatic structure chain related to alkyl) means a straight or branched-chain group containing from one to seven, preferably a maximum of four, carbon atoms such as methyl, ethyl, propyl, isopropyl, butyl, sec-butyl, t-butyl and pentyl. Optional substituents which may be present on the alkyl groups include one or more substituents selected from halogen, amino, monoalkylamino, dialkylamino, hydroxy, alkoxy, alkylthio, alkylsulphonyl, acylamino, alkoxycarbonylamino, alkanoyl, acyloxy, carboxyl, sulphate or phosphate groups. Examples of alkoxy groups are methoxy, ethoxy, propoxy, isopropoxy, butoxy and t-butoxy. The term "halogen" means fluorine, chlorine, bromine or iodine.

An alkenyl group is an olefinic group containing from two to seven carbon atoms for example methylene, ethylene, n-propylene, i-propylene, n-butylene, i-butylene, s-butylene and t-butylene. An alkynyl group is of a group of 2–7 carbon atoms for example ethynyl, propynyl or butynyl group.

The term aryl alone or in combination means an unsubstituted phenyl group or a phenyl group carrying one or more, preferably one to three, substituents examples of which are halogen, alkyl, haloalkyl, hydroxy, nitro, cyano, amino and alkoxy. A haloalkyl group can carry one or more halogen atoms with the examples of such groups being trifluoromethyl and dichloromethyl.

The term heteroaryl is defined herein as a mono- or bi-cyclic aromatic group containing one to four heteroatoms selected in any combination from N, S or O atoms and a maximum of 9 carbon atoms. Examples of heteroaryl groups include pyridyl, pyrimidyl, furyl, thienyl, pyrrolyl, pyrazolyl, indolyl, benzofuryl, benzothienyl, benzothiazolyl, oxazolyl, isoxazolyl, thiazolyl, isothiazolyl, imidazolyl, triazolyl, quinolyl and isoquinolyl groups.

The term aralkyl is defined herein as an alkyl group, as previously defined, in which one of the hydrogen atoms is replaced by an aryl or heteroaryl group as defined herein.

Where one or more functional groups in compounds of formulae I, II, IIA are sufficiently basic or acidic the formation of salts is possible. Suitable salts include pharmaceutically acceptable salts for example acid addition salts including hydrochlorides, hydrobromides, phosphates, sulphates, hydrogen sulphates, alkylsulphonates, arylsulphonates, acetates, benzoates, citrates, maleates, fumarates, succinates, lactates and tartrates, salts derived from inorganic bases including alkali metal salts such as sodium or potassium salts, alkaline earth metal salts such as magnesium or calcium salts, and salts derived from organic amines such as morpholine, piperidine or dimethylamine salts.

Those skilled in the art will recognise that compounds of formulae I, II, IIA may exist as stereoisomers and/or geometrical isomers and accordingly the present invention includes all such isomers and mixtures thereof.

One useful group of compounds includes those in which R₁, R₂ and R₃ are each alkyl.

Another useful group of compounds includes those in which R₁, R₂ and R₃ are each alkyl and R₅ and R₇ are each hydrogen. A particularly useful subset of this group includes compounds in which R₁, R₂ and R₃ are each methyl and R₆ is hydrogen, alkyl or PO₃H₂.

Particularly useful compounds according to the invention include:

N-Acetylcolchinol-O-phosphate and its salts, solvates and hydrates.

Compounds of formulae I, II or IIA may be prepared by a number of processes as generally described below and more specifically in the Examples hereinafter. In the following process description the symbols R₁, R₂, R₃, R₄, R₅, R₆ and R₇ when used in the formulae depicted are to be understood to represent those groups described above in relation to formulae I, II or IIA unless otherwise indicated. In the schemes described below it may be necessary to employ protecting groups which are then removed during the final stages of the synthesis. The appropriate use of such protecting groups and processes for their removal will be readily apparent to those skilled in the art.

Thus according to a further aspect of the invention compounds of formulae II or IIA in which R₅, R₆ and R₇ are each hydrogen may be prepared by treatment of a compound of formula (2) with alkaline hydrogen peroxide. The reaction may be conveniently performed in aqueous sodium hydroxide solution in the absence or presence of a cosolvent such as an alcohol, for example ethanol, at a temperature in the range for example 0–100° C. preferably at or near to 60° C.

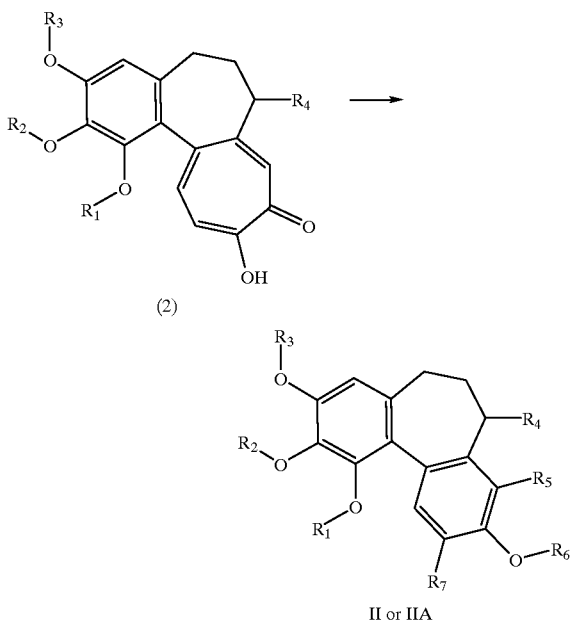

(2)

II or IIA

Intermediates of formulae (2) may be prepared by acid hydrolysis of compounds of formulae (3). The reaction is conveniently carried out in an aqueous acid such as hydrochloric acid at an elevated temperature, for example at or near 100° C.

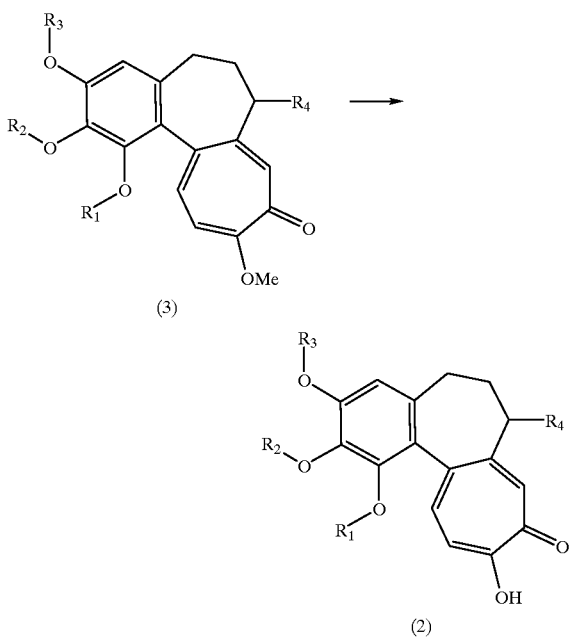

(3)

(2)

Compounds of formula (3) are either known or can be prepared from colchicine by conventional procedures.

Compounds of formulae I, II or IIA may also be prepared from other compounds of formulae I, II or IIA, by chemical modification. Examples of such chemical modifications that may be applied are standard alkylation, arylation, heteroarylation, acylation, thioacylation, sulphonylation, sulphation, phosphorylation, aromatic halogenation and coupling reactions. These reactions may be used to add new substituents or to modify existing substituents. Alternatively, existing substituents in compounds of formulae I, II or IIA may be modified by, for example oxidation, reduction, elimination, hydrolysis or other cleavage reaction to yield other compounds of formulae I, II or IIA.

Thus for example a compound of formulae II or IIA containing an amino group may be acylated on the amino group by treatment with, for example, an acyl halide or anhydride in the presence of a base, for example a tertiary amine base such as triethylamine, in for example, a solvent such as a hydrocarbon solvent e.g. dichloromethane at a temperature in the range for example −30° C. to 120° C., conveniently at or near ambient temperature.

In another general example of an interconversion process an amino group in a compound of formulae II or IIA may be sulphonylated by treatment with, for example, an alkyl or aryl sulphonyl chloride or an alkyl or aryl sulphonic anhydride in the presence of a base, for example a tertiary amine base such as triethylamine, in for example a solvent such as a hydrocarbon solvent e.g. dichloromethane at a temperature in the range for example −30° C. to 120° C., conveniently at or near ambient temperature.

In a further general example a compound of formulae II or IIA containing a hydroxy group can be converted into the corresponding dihydrogenphosphate ester by treatment with for example di-tert-butyl diethylphosphoramidite in the presence of a suitable catalyst for example tetrazole. In a solvent such as an ether solvent for example tetrahydrofuran at a temperature in the range −40 to 40° C., conveniently at or near room temperature, followed by treatment with an oxidising agent for example 3-chloroperoxy benzoic acid at a temperature in the range −78° C. to 40° C. preferably −40 to −10° C. The resulting intermediate phosphate triester is treated with an acid for example trifluoroacetic acid in a solvent such as a chlorinated solvent e.g. dichloromethane at a temperature in the range −30 to 40° C. conveniently at or near 0° C. to give the compound of formula (2) containing a dihydrogenphosphate ester.

In a further general example a compound of formula (2) containing an amide can be hydrolysed by treatment with for example an acid such as hydrochloric acid in a solvent such as an alcohol, for example methanol at an elevated temperature conveniently at the reflux temperature.

In another general example an O-alkyl group may be cleaved to the corresponding alcohol (OH) by reaction with boron cribromide in a solvent such as a chlorinated solvent e.g. dichioromethane at a low temperature e.g. around −78° C.

In a further general example compounds of formulae II or IIA may be alkylated by reaction with a suitable alkylating agent such as an alkyl halide, an alkyl toluenesulphonate, an alkyl methanesulphonate or an alkyl triflate. The alkylation reaction can be carried out in the presence of a base for example an inorganic base such as a carbonate e.g. caesium or potassium carbonate, a hydride such as solitaii hydride or an alkoxide such as potassium t-butoxide in a suitable solvent such as an aprotic solvent e.g. dimethylformamide or an ether solvent such as tetrahydrofuran at a temperature of around −10 to 80° C.

Preparation of a compound of formulae II or IIA as a single enantiomer or, where appropriate, diastereomer may be effected by synthesis from an enantiomerically pure starting material or intermediate or by resolution of the final product in a conventional manner.

Acid addition salts of the compounds of formulae II or IIA are prepared in a conventional manner by treating a solution or suspension of the free base II or IIA with about one equivalent of a pharmaceutically acceptable acid. Salts of compounds of formulae I, II or IIA derived from inorganic or organic bases are prepared in conventional manner by treating a solution or suspension of the free acid I, II or IIA with about one equivalent of a pharmaceutically acceptable organic or inorganic base. Alternatively both acid addition salts and salts derived from bases may be prepared by treatment of the parent compound with the appropriate ion-exchange resin in a standard fashion. Conventional concentration and recrystallisation techniques are employed in isolating the salts.

Compounds according to the invention are able to destroy tumour vasculature and vasculature that has been newly formed while leaving unaffected normal, mature vasculature. The ability of the compounds to act in this way may be determined by the tests described in the Examples hereinafter.

The compounds according to the invention are thus of particular use in the prophylaxis and treatment of cancers involving solid tumours and in the prophylaxis and treatment of diseases where inappropriate angiogenesis occurs such as diabetic retinopathy, psoriasis, rheumatoid arthritis, atherosclerosis and macular degeneration.

The compounds of the invention may be administered as a sole therapy or in combination with other treatments. For the treatment of solid tumours compounds of the invention may be administered in combination with radiotherapy or in combination with other anti-tumour substances for example those selected from mitotic inhibitors, for example vinblastine, paclitaxel and docetaxel; alkylating agents, for example cisplatin, carboplatin and cyclophosphamide, antimetabolites, for example 5-fluorouracil, cytosine arabinoside and hydroxyurea; intercalating agents for example adriamycin and bleomycin; enzymes, for example asparaginase; topoisomerase inhibitors for example etoposide, topotecan and irinotecan; thymidylate synthase inhibitors for example raltitrexed; biological response modifiers for example interferon; antibodies for example edrecolomab, and anti-hormones for example tamoxifen. Such combination treatment may involve simultaneous or sequential application of the individual components of the treatment.

For the prophylaxis and treatment of disease the compounds according to the invention may be administered as pharmaceutical compositions selected with regard to the intended route of administration and standard pharmaceutical practice. Such pharmaceutical compositions may take a form suitable for oral, buccal, nasal, topical, rectal or parenteral administration and may be prepared in a conventional manner using conventional excipients. For example for oral administration the pharmaceutical compositions may take the form of tablets or capsules. For nasal administration or administration by inhalation the compounds may be conveniently delivered as a powder or in solution. Topical administration may be as an ointment or cream and rectal administration may be as a suppository. For parenteral injection (including intravenous, subcutaneous, intramuscular, intravascular or infusion) the composition may take the form of, for example, a sterile solution, suspension or emulsion.

The dose of a compound of the invention required for the prophylaxis or treatment of a particular condition will vary depending on the compound chosen, the route of administration, the form and severity of the condition and whether the compound is to be administered alone or in combination with another drug. Thus the precise dose will be determined by the administering physician but in general daily dosages may be in the range 0.001 to 100 mg/kg preferably 0.1 to 50 mg/kg.

BIOLOGICAL ACTIVITY

The following tests were used to demonstrate the activity and selectivity of compounds according to the invention.
Activity Against Tumour Vasculature Measured by Radioactive Tracer.

The following experiment demonstrates the ability of the compounds to damage selectively tumour vasculature.

Subcutaneous CaNT tumours were initiated by injecting 0.05 ml of a crude tumour cell suspension, approximately $10^6$ cells, under the skin overlying the rear dorsum of 12–16 week-old mice. The animals were selected for treatment after approximately 3–4 weeks, when their tumours reached a geometric mean diameter of 5.5–6.5 mm. Compounds were dissolved in sterile saline and injected intraperitoneally in a volume of 0.1 ml per 10 g body weight. Tumour perfusion was measured 6 hours after intraperitoneal administration in tumour, kidney, liver, skin muscle, gut and brain by the $^{86}$RbCI extraction technique (Sapirstein, Amer J Physiol, 193, 161–168, 1958). Tissue radioactivity measured 1 minute after an intravenous injection of $^{86}$RbCI was used to calculate relative blood flow as a proportion of cardiac output (Hill and Denekamp, Brit J Radiol, 55, 905–913, 1982). Five animals were used in control and treated groups. Results were expressed as a percentage of the blood flow in the corresponding tissues in vehicle treated animals.
Activity Against Tumour Vasculature Measured by Fluorescent Dye.

The following experiment further demonstrates the ability of the compounds to damage tumour vasculature.

Tumour functional vascular volume in CaNT tumour-bearing ice was measured using the florescent dye Hoechst 33342 according to the method of Smith et al (Brit J Cancer 57, 247–253, 1988). Five animals were used in control and treated groups. The fluorescent dye was dissolved in saline at 6.25 mg/ml and injected intravenously at 10 mg/kg 6 hours after intraperitoneal drug treatment. One minute later, animals were killed and tumours excised and frozen; 10 $\mu$m sections were cut at 3 different levels and observed under UV illumination using an Olympus microscope equipped with epifluorescence. Blood vessels were identified by their fluorescent outlines and vascular volume was quantified using a point scoring system based on that described by Chalkley, (J Natl Cancer Inst, 4, 47–53, 1943). All estimates were based on counting a minimum of 100 fields from sections cut at the 3 different levels. Compounds of the invention reduced tumour functional vascular volume by greater than 20% at doses of 50 mg/kg or below.

The following non-limiting Examples illustrate the invention. In the Examples all $_1$Hnmr were run at 300 MHz unless otherwise specified. Column chromatography was performed on silica gel. All temperatures are in ° C. The following abbreviations are used: THF—tetrahydrofuran; DMSO—dimethylsulphoxide; MCPBA—3-chloroperoxlybenzoic acid.

EXAMPLE 1

N-Acetylcolchinol-O-phosphate

A solution of N-acetylcolchinol (260 mg, 0.76 mmol) in anhydrous THF (2 ml) under an atmosphere of nitrogen-was treated with di-t-butyl diethylphosphoramidite (189 mg, 0.75 mmol) and 1(H)-tetrazole (0.14 g, 1.99 mmol) and the solution stirred at 200 for 0.5 h. The solution was cooled to −40° and a solution of 85% MCPBA (202 mg, 0.99 mmol) in anhydrous dichloromethane (2 ml) at such a rate that the temperature remained below −10°. The solution was allowed to warm to room temperature, diethyl ether (30 ml) was added and the resulting solution washed successively with 10% aqueous sodium metabisulphite (two 25 ml portions), 5% aqueous sodium bicarbonate (two 25 ml portions), 5% aqueous citric acid (30 ml), 5% aqueous sodium bicarbonate, and brine. The organic solution was concentrated under reduced pressure and the residue subjected to column chromatography to afford a white foam (170 mg) containing N-acetylcolchinol-O-di-t-butylphosphate which was redissolved in dichloromethane (5 ml), cooled to 0° and treated with trifluoroacetic acid (0.5 ml).

The solution was allowed to warm to room temperature and stir 1 hr before being concentrated under reduced pressure and triturated with ether to give the title compound (110 mg) as a white solid m.p. 233–235°. δH (d6-DMSO) 8.38(d,1H, J=8 Hz), 7.27(d, 1H,J=7 Hz), 7.12(d, 1H, J=8 Hz), 7.10(s,1H), 6.77 (s, 1H), 4.48 (m, 1H), 3.81 (s, 3H), 3.76 (s, 3H), 3.49 (s, 3H), 2.5 (signal partially obscured by DMSO peak), 1.9–2.2 (m, 2H), 1.86 (s, 3H).

The activity of the phosphate compound was measured by the radioactive tracer assay described above: the compound of this Example gave a 65% decrease in tumour blood flow at a dose of 125 mg/kg with no significant reduction in blood flow in skin, muscle, liver, kidney, gut or heart.

The phosphate compound was compared with the parent N-acetylcolchinol for the maximum tolerated dose (MTD) (no deaths in three animals), minimum effective dose (MED) measured by the fluorescent dye technique already described and the therapeutic window (MTD/MED).

|  | MTD mg/Kg body weight | MED mg/Kg body weight | Therapeutic Window (MTD/MED) |
|---|---|---|---|
| N-acetyl colchinol | 125 | 30 | 4 |
| N-acetyl colchinol-O-phosphate | 750 | 50 | 15 |

Though the phosphate had a slightly higher MED the "window" was significantly greater. This was unexpected. The phosphate also gave greater solubility.

For comparison the "therapeutic windows" for colchicine (the closest structure to the present compounds and docetaxel (a tubulin-binding drug, marketed as "Taxotere", which has no vascular-damaging activity) and these data are presented in the following table:

TABLE 1

Therapeutic windows of other tubulin-binding agents (by fluorescent dye technique)

| Compound | MED (mg/kg body weight) | MTD (mg/kg body weight) | MTD/MED |
|---|---|---|---|
| Docetaxel | >30 (No effect at 30) | 30 | <1 |
| Colchicine | 2.5 | 5 | 2 |

EXAMPLE 2

N-Ethylcolchinol

A solution of N-acetylcolchinol (500 mg, 1.4 mmol) in THF (15 ml) was added dropwise over 15 minutes to a suspension of lithium aluminum hydride (106 mg, 2.74 mmol) in THF (10 ml) with ice-bath cooling. The mixture was heated at reflux for 15 h, allowed to cool and treated with further lithium aluminium hydride (53 mg, 1.4 mmol) before heating at reflux for a further 3 h. The mixture was cooled (ice bath) and water (10 ml) added dropwise before extraction with three portions of ethyl acetate. The combined, dried (MgSO4) extracts were concentrated under reduced pressure to a green gum which, on trituration with ether, gave the title compound as a light-green solid. m.p. 185° C. (dec.), m/e 343 (M+). Anal. Calculated for $C_{20}H_{25}NO_4$ $H_2O$: C, 66.46; H, 7.53; N, 3.88. Found: C, 66.50; H. 7.17; N, 3.79.

EXAMPLE 3

N-Benzyloxycarbonylcolchinol

A solution of colchinol (625 mg, 1.98 mmol) in dry pyridine (10 ml) was treated dropwise with benzylchloroformate (0.566 ml, 3.97 mmol) and the mixture stirred 16 h. Solvent was removed under reduced pressure, water added and the resulting mixture extracted with three portions of chloroform. The combined, dried ($MgSO_4$) extracts were concentrated under reduced pressure to a dark brown gum which was subjected to column chromatography on silica gel eluting with 50% ethyl acetate/petroleum ether. The resultant orange gum was crystallised from ether/petroleum ether to give the title compound (346 mg) as a pale yellow solid. m.p. 79–81° C., m/e 449 (M+). Anal. Calculated for $C_{26}H_{27}NO_6$ $0.33H_2O$; C, 68.57; H, 6.07; N, 3.08. Found: C, 68.71; H, 6.18; N, 2.91.

EXAMPLE 4

N-(Phenylcarbamoyl) colchinol

A solution of colchinol (400 mg, 1.27 mmol) in dry pyridine (10 ml) was treated dropwise with phenyl isocyanate (0.151 ml, 1.39 mmol) and the mixture stirred for 18 h before heating at reflux for 2 h. Solvent was removed under reduced pressure, water added and the resulting mixture extracted with three portions of chloroform. The combined, dried ($MgSO_4$) extracts were concentrated under reduced pressure to a dark brown gum which was subjected to column chromatography on silica gel eluting with 35% ethyl acetate/petroleum ether. The resultant gum was crystallised from ether/petroleum ether to give the title compound (261 mg) as a pale orange solid. m.p. 145–146° C., m/e 434 (M+).

EXAMPLE 5

N-Mesylcolchinol

A solution of N,O-dimesylcolchinol (234 mg, 0.5 mmol) in methanol (8 ml) was treated with sodium hydroxide (40 mg, 1 mmol) and the mixture heated at reflux for 3 h. Solvent was removed under reduced pressure and water (5 ml) added. The solution was rendered neutral by the addition of 1M hydrochloric acid and extracted with three portions of dichloromethane. The combined, dried ($MgSO_4$) extracts were concentrated under reduced pressure to give the title compound (123 mg) as a pink solid. m.p. 234–236° C., m/e 393 (M+).

The N,O-dimesylcolchinol used as starting material was prepared as follows: A solution of colchinol (500 mg, 1.6 mmol) in dry pyridine (15 ml) was treated with mesyl chloride (0.135 ml, 1.7 mmol) and the mixture stirred at room temperature 36 h. A further portion of mesyl chloride (0.135 ml, 1.7 mmol) was added and stirring continued 16 h. Solvent was removed under reduced pressure and water (5 ml) added. The solution was extracted with three portions of chloroform and the combined, dried ($MgSO_4$) extracts were concentrated under reduced pressure to give a brown gum which was subjected to column chromatography on silica gel eluting with ethyl acetate to give N,O-dimesylcoichinol (292 mg) as a light orange solid.

EXAMPLE 6
N-Dimethylsulphamoylcolchinol

A solution of colchinol (50 mg, 0.16 mmol) in dry acetonitrile (3 ml) and triethylamine (0.022 ml, 0.16 mmol) was treated with dimethylsulphamoyl chloride and the mixture stirred for 30 minutes before heating at reflux for 15 h. Solvent was removed under reduced pressure, water added and the resulting mixture extracted with three portions of chloroform. The combined, dried ($Na_2SO_4$) extracts were concentrated under reduced pressure to a dark brown gum which was subjected to column chromatography on silica gel eluting with ethyl acetate to give the title compound (46 mg) as a pale orange gum which solidified. m.p. 82–85° C. m/e 422 (M+).

EXAMPLE 7
N-Acetyl-O-methoxycarbonylmethylcolchinol

A solution of N-acetylcolchinol (500 mg, 1.4 mmol) in dry DMF (5 ml) at 0° C. was treated with methylbromoacetate (322 mg, 2.1 mmol) and sodium hydride (84 mg of a 60% suspension in oil, 2.1 mmol) and the mixture stirred for 30 minutes. Water (50 ml) was added and the mixture extracted with four portions of ethyl acetate. The combined extracts were washed successively with four portions of water and two portions of saturated aqueous sodium chloride solution, dried ($MgSO_4$) and solvent removed under reduced pressure to give the title compound (280 mg) as a white solid m.p. 82–83° C. m/e 429 2 (M+). Anal. Calculated for $C_{23}H_{27}NO_7$ $0.33H_2O$; C, 63.45; H, 6.40; N, 3.22. Found: C, 63.53; H, 6.29; N, 3.17.

EXAMPLE 8
N-Acetyl-O-carboxymethylcolchinol

A solution of N-acetyl-O-methoxycarbonylmethylcolchinol (140 mg, 0.33 mmol) in acetonitrile (5 ml) was treated with aqueous potassium hydroxide solution (1.0M, 5 ml) and the mixture heated at 80° C. for 30 minutes. The cooled mixture was adjusted to pH3 by addition of 2M hydrochloric acid and extracted with four portions of ethyl acetate. The combined extracts were washed with two portions of saturated aqueous sodium chloride solution, dried ($MgSO_4$) and concentrated under reduced pressure. Addition of acetone (2 ml) and hexane (1 ml) produced the title compound (58 mg) as a white solid m.p. 220–221° C. m/e 415.3 (M+). Anal. Calculated for $C_{22}H_{25}NO_7$ $0.33H_2O$; C,62.71; H, 6.14; N, 3.32. Found: C, 62.63; H, 6.02; N, 3.26.

EXAMPLE 9
N-Acetyl-O-cyclopentylcolchinol

A solution of N-acetylcolchinol (200 mg, 0.56 mmol) in dry DMF (2 ml) at 0° C. was treated with sodium hydride (33 mg of a 60% suspension in oil, 0.84 mmol) followed by cyclopentyl bromide (125 mg, 0.84 mmol) and the mixture stirred 1 h. A further portion of sodium hydride (17 mg of a 60% suspension in oil, 0.42 mmol) and of cyclopentyl bromide (63 mg, 0.42 mmol) and the mixture stirred overnight at room temperature. Water (10 ml) was added and the mixture extracted with four portions of ethyl acetate. The combined extracts were washed with two portions of saturated aqueous sodium chloride solution, dried ($MgSO_4$) and concentrated under reduced pressure. The title compound (160 mg) was obtained as a white solid m.p. 89–94° C. m/e 425.3 (M+). Anal. Calculated for $C_{25}H_{31}NO_5$: C, 70.54; H, 7.35; N, 3.29. Found: C, 70.55; H, 7.35; N, 3.25.

EXAMPLE 10

N-Acetyl-10-nitrocolchinol

A solution of N-acetylcolchinol (100 mg, 0.27 mmol) in glacial acetic acid (20 ml) was treated slowly with 20 ml of a solution of concentrated nitric acid (0.34 ml) in acetic acid (100 ml) keeping the temperature at about 12° C. The mixture was stirred at room temperature for 18 h, a further 1 ml of the nitric acid/acetic acid solution added and stirring continued for 2 h. The mixture was poured onto ice and extracted with three portions of ethyl acetate. The combined extracts were washed with two portions of saturated aqueous sodium cloride solution, dried ($MgSO_4$) and concentrated under reduced pressure. Purification on silica gel eluting with ethyl acetate gave the title compound (50 mg) as a pale yellow solid m.p. 117–8° C. m/e 401.9 (M+) Anal. Calculated for $C_{20}H_{22}N_2O_7$ $0.33H_2O$; C, 58.82; H, 5.56; N, 6.86. Found: C, 58.87; H, 5.66; N, 6.55.

EXAMPLE 11

The activity against tumour vasculature was measured by the fluorescent dye technique described above for the compounds of Examples 1–10 administered at 50 mg/kg and N-acetylcolchinol

| Compound of Example | % decrease in vascular volume |
|---|---|
| 1 | 89 |
| 2 | 38 |
| 3 | 43 |
| 4 | 37 |
| 5 | 38 |
| 6 | 30 |
| 7 | 12 |
| 8 | 49 |
| 9 | 59 |
| 10 | 28 |
| N-acetylcolchinol | 78 |

What is claimed is:

1. A method for the treatment of a disease where inappropriate angiogenesis occurs in a warm-blooded animal comprising administering to said animal a compound of the formula

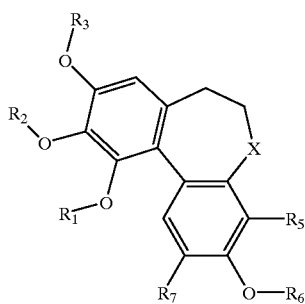

(I)

wherein
R$_1$, R$_2$, R$_3$ and R$_6$ are each independently H, optionally substituted alkyl, cycloalkyl, alkenyl, alkynyl, aralkyl, alkanoyl, PO$_3$H$_2$;

X is carbonyl (CO), thiocarbonyl (CS), methylene (CH$_2$) or a group CHR$_4$;

R$_4$ is OH, O-alkyl or NR$_8$R$_9$;

R$_5$ and R$_7$ are each independently H, alkyl, halogen, hydroxy, alkoxy, nitro or amino;

R$_8$ is H, optionally substituted alkyl, cycloalkyl, alkanoyl, thioalkanoyl, aryl, heteroaryl, arylcarbonyl, heteroarylcarbonyl, alkoxycarbonyl, aryloxycarbonyl, aminocarbonyl, alkylaminocarbonyl, dialkylaminocarbonyl, arylaminocarbonyl, alkylsulphonyl, arylsulphonyl, aminosulphonyl, alkylaminosulphonyl, dialkylaminosulphonyl or arylaminosulphonyl; and R$_9$ is H, alkyl or cycloalkyl;

and the pharmaceutically acceptable salts, solvates and hydrates thereof.

2. The method according to claim 1 wherein at least one of R$_1$, R$_2$, R$_3$ and R$_6$ is PO$_3$H$_2$.

3. The method according to claim 2 wherein R$_6$ is PO$_3$H$_2$.

4. The method according to any one of claims 1 to 3 in which R$_1$, R$_2$ and R$_3$ are alkyl.

5. The method according to any one of claims 1 to 3 in which R$_4$ is acylamino.

6. The method according to claim 1 in which R$_6$ is PO$_3$H$_2$, R$_1$, R$_2$ and R$_3$ are alkyl and R$_4$ is acylamino.

7. A compound of the formula

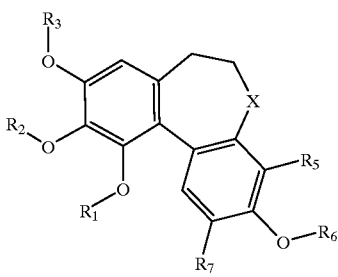

(I)

wherein
R$_1$, R$_2$, R$_3$ and R$_6$ are each independently H, optionally substituted alkyl, cycloalkyl, alkenyl, alkynyl, aralkyl, alkanoyl or PO$_3$H$_2$, provided that at least one of R$_1$, R$_2$, R$_3$ and R$_6$ is PO$_3$H$_2$;

X is carbonyl (CO), thiocarbonyl (CS), methylene (CH$_2$) or a group CHR$_4$;

R$_4$ is OH, O-alkyl or NR$_8$R$_9$;

R$_5$ and R$_7$ are each independently H, alkyl, halogen, hydroxy, alkoxy, nitro or amino;

R$_8$ is H, optionally substituted alkyl, cycloalkyl, alkanoyl, thioalkanoyl, aryl, heteroaryl, arylcarbonyl, heteroarylcarbonyl, alkoxycarbonyl, aryloxycarbonyl, aminocarbonyl, alkylaminocarbonyl, dialkylaminocarbonyl, arylaminocarbonyl, alkylsulphonyl, arylsulphonyl, aminosulphonyl, alkylaminosulphonyl, dialkylaminosulphonyl or arylaminosulphonyl; and R$_9$ is H, alkyl or cycloalkyl;

and pharmaceutically acceptable salts, solvates, and hydrates thereof.

8. The compound according to claim 7 in which R$_6$ is PO$_3$H$_2$.

9. The compound according to claim 8 in which R$_1$, R$_2$ and R$_3$ are alkyl and R$_4$ is acylamino.

10. A compound of the formula

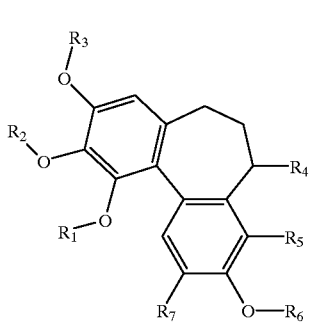

(II)

wherein
R$_1$, R$_2$ and R$_3$ are each independently H, optionally substituted alkyl, cycloalkyl, alkenyl, alkynyl, alkanoyl, or PO$_3$H$_2$;

R$_6$ is PO$_3$H$_2$;

R$_4$ is H or NR$_8$R$_9$;

R$_5$ and R$_7$ are each independently H, alkyl, halogen, alkoxy, nitro or amino;

R$_8$ is H, optionally substituted alkyl, cycloalkyl, alkanoyl, thioalkanoyl, aryl, heteroaryl, arylcarbonyl, heteroarylcarbonyl, alkoxycarbonyl, aryloxycarbonyl, aminocarbonyl, alkylaminocarbonyl, dialkylaminocarbonyl, arylaminocarbonyl, alkylsulphonyl, arylsulphonyl, aminosulphonyl, alkyaminosulphonyl, dialkylaminosulphonyl or arylaminosulphonyl; and R$_9$ is H, alkyl or cycloalkyl;

and pharmaceutically acceptable salts, solvates and hydrates thereof.

11. A compound of the formula

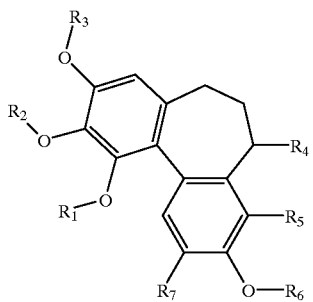

(IIA)

wherein
- $R_1$, $R_2$ and $R_3$ are each independently H, optionally substituted alkyl, cycloalkyl, alkenyl, alkynyl, alkanoyl or $PO_3H_2$;
- $R_6$ is H, optionally substituted alkyl, cycloalkyl, alkenyl, alkynyl or $PO_3H_2$;
- $R_4$ is H or $NR_8R_9$;
- $R_5$ and $R_7$ are each independently H, alkyl, halogen, nitro or amino;
- $R_8$ is H, optionally substituted alkyl, cycloalkyl, alkanoyl, thioalkanoyl, aryl, heteroaryl, arylcarbonyl, heteroarylcarbonyl, alkoxycarbonyl, aryloxycarbonyl, aminocarbonyl, alkylaminocarbonyl, dialkylaminocarbonyl, arylaminocarbonyl, alkylsulphonyl, arylsulphonyl, aminosulphonyl, alkylaminosulphonyl, dialkylaminosulphonyl or arylaminosulphonyl; and
- $R_9$ is H, alkyl or cycloalkyl;

with the proviso that, when $R_1$, $R_2$ and $R_3$ are all methyl groups and $R_4$ is hydrogen, acetylamino, acetylmethylamino, amino, methylamino or dimethylamino then $R_6$ is not hydrogen, methyl, hydroxyethyl, or acetoxyethyl;

and pharmaceutically acceptable salts, solvates and hydrates thereof.

12. A compound according to claim 11 in which $R_1$, $R_2$ and $R_3$ are alkyl and $R_4$ is acylamino.

13. A pharmaceutical composition comprising a compound according to any one of claims 7 to 12 and a pharmaceutically acceptable excipient.

14. A pharmaceutical composition according to claim 13 wherein the compound is N-acetylcolchinol-O-phosphate.

15. The compound N-acetylcolchinol-O-phosphate, or a salt, solvate or hydrate thereof.

16. A process for the preparation of a compound of formula II or IIA as claimed in claim 10 or 11, said process comprising treatment of a compound of formula (2) with alkaline hydrogen peroxide

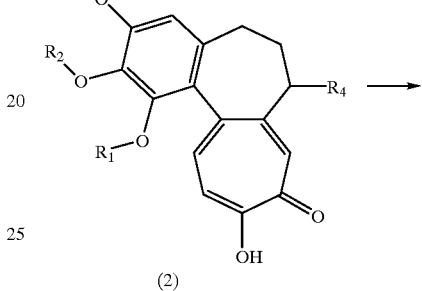

(2)

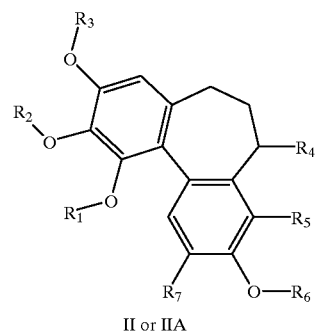

II or IIA wherein $R_1$, $R_2$, $R_3$, $R_4$, $R_5$, $R_6$ and $R_7$ are as defined in claim 10 or 11.

* * * * *